United States Patent
Mc Gowan, Sr. et al.

(10) Patent No.: US 7,766,904 B2
(45) Date of Patent: Aug. 3, 2010

(54) ADJUSTABLE LASER PROBE FOR USE IN VITREORETINAL SURGERY

(75) Inventors: Michael J. Mc Gowan, Sr., Barrington, NJ (US); Charles R. Hurst, Jr., Bullard, TX (US); Harry Michael Lambert, Houston, TX (US); Christopher F. Lumpkin, Evergreen, CO (US)

(73) Assignee: IRIDEX Corporation, Mountain View, CA (US)

( * ) Notice: Subject to any disclaimer, the term of this patent is extended or adjusted under 35 U.S.C. 154(b) by 898 days.

(21) Appl. No.: 11/035,694

(22) Filed: Jan. 14, 2005

(65) Prior Publication Data

US 2005/0154379 A1    Jul. 14, 2005

Related U.S. Application Data

(63) Continuation of application No. 10/765,350, filed on Jan. 27, 2004, now abandoned.

(60) Provisional application No. 60/444,060, filed on Jan. 31, 2003.

(51) Int. Cl.
*A61B 18/18* (2006.01)

(52) U.S. Cl. .......................... 606/13; 606/16

(58) Field of Classification Search .......... 606/4–6, 606/13–16, 166; 607/88, 89; 600/101–104, 600/114

See application file for complete search history.

(56) References Cited

U.S. PATENT DOCUMENTS

| | | | |
|---|---|---|---|
| 4,347,837 A | 9/1982 | Hosono | |
| 4,674,497 A | 6/1987 | Ogasawara | |
| 4,744,360 A | 5/1988 | Bath | |
| 5,172,685 A | 12/1992 | Nudelman | |
| 5,281,214 A * | 1/1994 | Wilkins et al. | 606/15 |
| 5,300,061 A | 4/1994 | Easley et al. | |
| 5,372,585 A | 12/1994 | Tiefenbrun et al. | |
| 5,469,524 A * | 11/1995 | Esch et al. | 385/118 |
| 5,512,034 A | 4/1996 | Finn et al. | |
| 5,520,222 A | 5/1996 | Chikama | |
| 5,549,565 A | 8/1996 | Ryan et al. | |
| 5,603,710 A | 2/1997 | Easley | |
| 5,656,011 A | 8/1997 | Uihlein et al. | |
| 5,688,264 A | 11/1997 | Ren et al. | |
| 5,735,792 A | 4/1998 | Vanden Hoek et al. | |

(Continued)

FOREIGN PATENT DOCUMENTS

DE        198 24 796 A1    1/1999

(Continued)

*Primary Examiner*—Ahmed M Farah
(74) *Attorney, Agent, or Firm*—Sterne, Kessler, Goldstein & Fox P.L.L.C.

(57) ABSTRACT

A laser probe including a handpiece and a rigid cannula fixed to the handpiece to prevent relative translational movement-therebetween. An optical fiber for delivering laser energy is supported for translational movement relative to the handpiece. A slidable button is fixed to the optical fiber via a rigid sleeve such that the button and optical fiber move together in the same direction during operation. The fiber may be selectively positioned relative to the button to cause the button to act as a visual indicator of the direction in which the fiber will extend from the cannula. The button may be specially configured with an enlarged head portion to enhance grippability and smooth operation of the button.

24 Claims, 7 Drawing Sheets

U.S. PATENT DOCUMENTS

| | | |
|---|---|---|
| 5,741,225 A | 4/1998 | Lax et al. |
| 5,766,164 A | 6/1998 | Mueller et al. |
| 5,807,242 A | 9/1998 | Scheller et al. |
| 5,807,424 A * | 9/1998 | de Ruiter et al. ............... 95/148 |
| 5,855,577 A * | 1/1999 | Murphy-Chutorian et al. . 606/7 |
| 5,993,072 A | 11/1999 | De Juan et al. |
| RE36,473 E * | 12/1999 | Esch et al. .................. 385/118 |
| 6,053,911 A | 4/2000 | Ryan et al. |
| 6,129,721 A | 10/2000 | Kataoka et al. |
| 6,142,990 A | 11/2000 | Burk |
| 6,572,608 B1 * | 6/2003 | Lee et al. ...................... 606/15 |
| 6,575,989 B1 | 6/2003 | Scheller et al. |
| 6,984,230 B2 * | 1/2006 | Scheller et al. ............... 606/15 |

FOREIGN PATENT DOCUMENTS

| | | |
|---|---|---|
| WO | WO 95/31926 | 11/1995 |

* cited by examiner

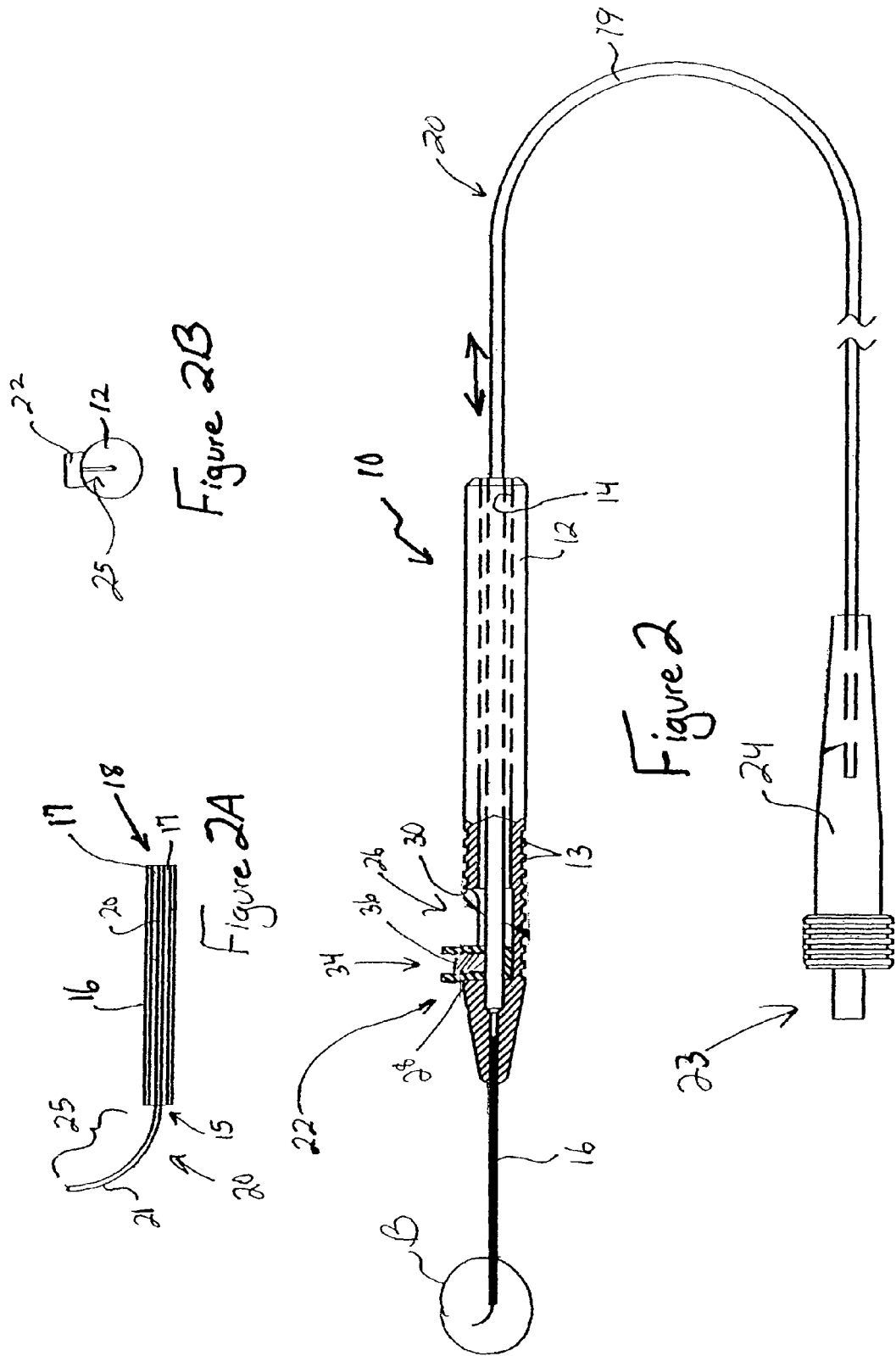

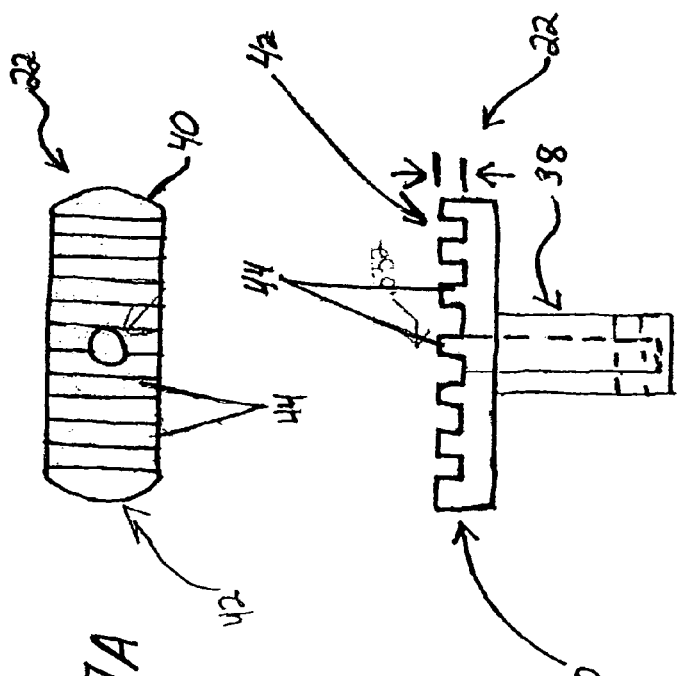
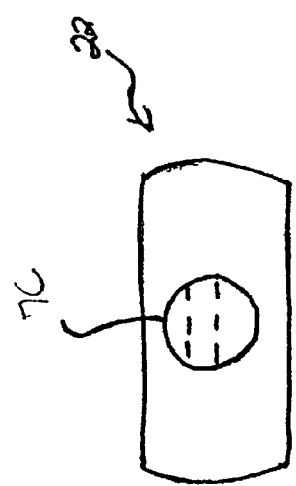
Figure 7A
Figure 7B
Figure 7C

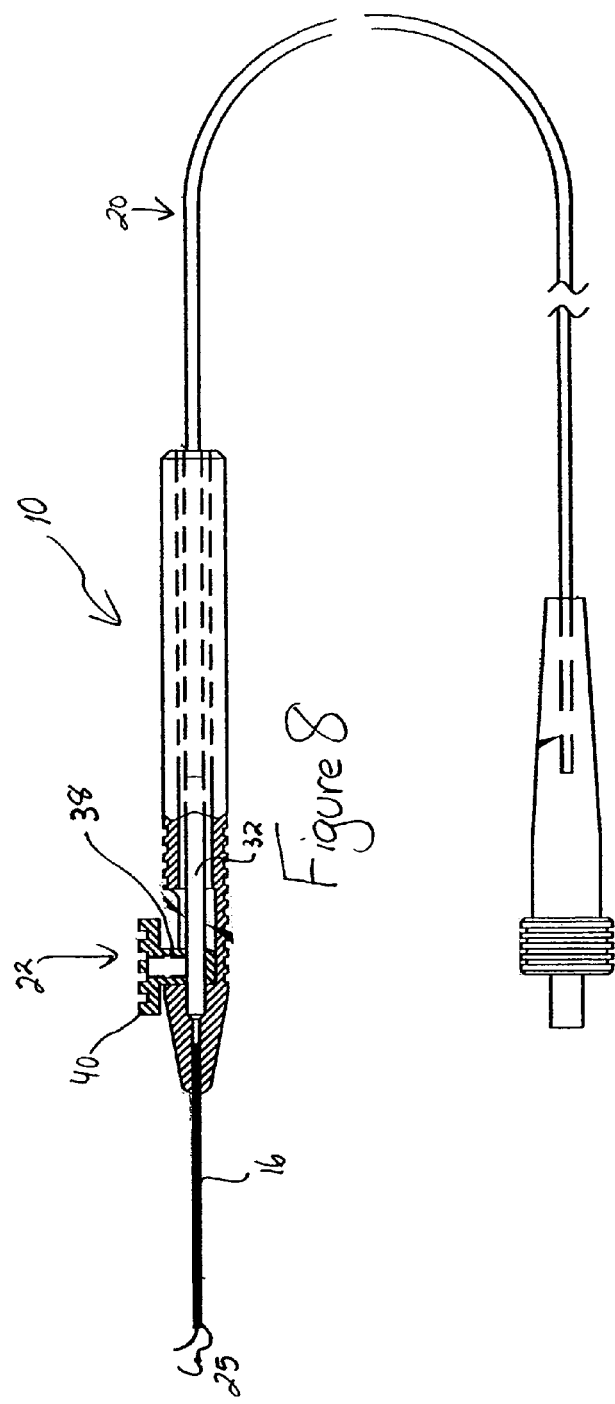
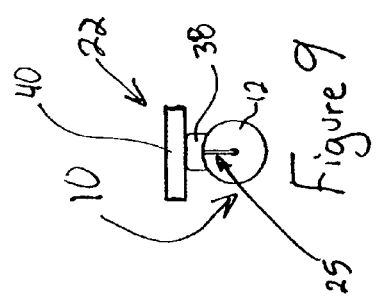

ADJUSTABLE LASER PROBE FOR USE IN VITREORETINAL SURGERY

CROSS-REFERENCE TO RELATED APPLICATION

This application claims the benefit of U.S. Provisional Patent Application No. 60/444,060, filed Jan. 31, 2003, the entire disclosure of which is hereby incorporated herein by reference.

FIELD OF THE INVENTION

The present invention relates generally to laser probes, and more particularly to an adjustable laser probe for effecting laser-induced photocoagulation to treat areas internal to the eye during vitreoretinal surgery.

DISCUSSION OF RELATED ART

A vitreoretinal specialist is an ophthalmic surgeon specializing in the diagnosis and treatment of the retina and vitreous. A vitreoretinal surgeon is often called upon to perform a vitrectomy procedure, which typically involves making three stab incisions for access to the posterior segment (back part) of the eye, i.e. the vitreous cavity. One of those incisions (inferio-temporally) is ultimately used for insertion of an infusion cannula, which is used during surgery to introduce fluids to prevent collapse and otherwise maintain integrity of the eye. The other incisions are needed for insertion of specific surgical instruments. Typical incisions in vitreoretinal surgery are slit-like stab incisions approximately 20 gauge (g) in size. A 20 g incision will usually allow an instrument having a 20 g shaft to be inserted into the eye. Size also refers to the diameter of the tubular shaft of the instrument at both the proximal and distal aspects of the inserted portion of the instrument. Instruments that are used in vitreoretinal surgery typically range in size from 18 g to 42 g.

Some surgical techniques involve use of tracer cannulae for the protection of both internal and external surrounding ocular tissues, for repositioning the infusion cannula to access areas of the eye that are difficult to reach, and for more readily inserting surgical instruments into the eye. These cannulae are positioned inside the incision, extending both internally and externally to the eye, and are left in place during the procedure. They act as a conduit, holding the incision open. The most commonly used sizes of tracer cannulae are 19 g, 20 g and 25 g. The "gauge size" refers to the size of the instrument that will pass through the cannula without interference. These cannulae are rigid and do not allow instruments with working ends larger than the diameter size to pass through.

Vitreoretinal surgeons routinely perform laser-induced photocoagulation of the retina. This procedure can be done in both the office treatment room and the operating room. Photocoagulation is accomplished with either an argon (green) or diode (infrared) wavelength laser. In the office setting, this is performed with the use of a "slit lamp," an illuminating microscope that also allows the application of laser energy when appropriately equipped. During vitreous surgery in the operating room, an endo ocular laser probe is the most commonly used method to deliver the laser energy. The endo ocular laser probe is inserted into the eye and an aiming beam emitted from the probe helps the surgeon to properly position the probe to the desired treatment area. Laser probe types include laser delivery, illuminating and aspirating. Typical laser delivery laser probes may have either fixed straight, or fixed curved configurations.

Both straight and curved probes have distinct benefits and limitations. A straight endoprobe will benefit the surgeon when he needs to apply laser energy straight on, directly to the posterior area of the retina. However, a straight endoprobe's effectiveness is limited when the surgeon needs to apply laser energy to the peripheral areas of the retina. On the other hand, a curved endoprobe will aid the surgeon when laser energy is needed in the peripheral area of the retina, where a straight probe cannot reach. The curved endoprobe is most limited when laser energy is needed in the posterior area of the retina, where a straight probe would be ideal. Additionally, while a straight probe will fit through a straight trocar cannula, a curved probe will not.

In many instances, the surgeon will require the hospital to maintain in inventory both straight and curved laser probes. This results in added cost to the patient and hospital, requires additional shelf space to store both types of probes, and results in more time to complete the vitrectomy.

An adjustable laser probe is being sold by Synergetics, Inc. of St. Charles, Mo. (Model No. 55.26, accessible via http://www.synergeticsusa.com), as shown in FIGS. 1A-1D. A similar laser probe is disclosed in U.S. Pat. No. 6,572,608 to Lee et al., the disclosure of which is hereby incorporated herein by reference. These laser probes are selectively adjustable to cause the fiber to bend to provide both straight and curved configurations. Referring now to the exemplary device shown in FIGS. 1A-1D, the laser probe 2 includes a handpiece 4 supporting an optical fiber 6 for delivering laser energy. The optical fiber 6 is fixed in position relative to the handpiece 4. The distal end 7 of the fiber 6 is positioned within a "pre-bent" flexible tube of nitinol 9 (memory metal) that is curved to about 90 degrees at its distal end when in a relaxed state, as best shown in FIG. 1C. The handpiece 4 also supports a straight, non-flexible (rigid) sheath 8 that is extendable and retractable relative to the handpiece 4. The sheath 8 may be extended or retracted by manipulating a button 3 that is fixedly attached directly to the sheath 8, as best shown in FIG. 1D. Specifically, the button 3 may be advanced to extend the sheath 8 relative to the handpiece 4 to enclose the fiber 6, thereby straightening the fiber as shown in FIG. 1A, or the button 3 may be retracted to retract the sheath 8 relative to the handpiece 4, thereby exposing the fiber 6 and allowing it to curl into the curved tip configuration (FIGS. 1B, 1C and 1D).

In use, a surgeon advances the button 3 and sheath 8 to straighten the fiber 6 before introduction of the probe 2 into the eye, and prior to removal of the probe 2 from the eye. This allows the probe 2 to pass through an incision in the eye without damaging ocular tissue. Once inside the eye, the surgeon retracts the button 3 and rigid sheath 8 to allow the flexible fiber 6 to return to the curved configuration, which varies up to about 90 degrees.

With such a probe, the surgeon must continually keep a finger positioned on the slidable button since the sheath 8 is movable independent of the probe's handpiece 4. Additionally, the configuration of the probe is dangerous to a patient in that it operates in a manner that may result in damage to the patient's ocular tissue in unexpected circumstances, e.g. during quick withdrawal from the eye as when a patient "startles" under anesthesia. More specifically, a surgeon's reaction to such circumstances often results in retraction of probe 2/handpiece 4 from the eye, and retraction of the button 3 relative to the handpiece. Such retraction of the button 3 results in retraction of the sheath 8 and corresponding exposure of the fiber 6 in the curved tip configuration. Withdrawing the probe from the eye with the fiber in the curved tip configuration will cause ocular tissue to be damaged as the probe is withdrawn. Accordingly, it is disadvantageous and dangerous to require advancement of the button 3 and sheath 8 (in a certain direction) at the time of withdrawal of the probe from the eye (in an opposite direction) in order to prevent damage to ocular tissue. What is needed is an adjustable laser probe providing straight and curved tip configurations while eliminating or reducing such disadvantages.

SUMMARY

The present invention provides an endo ocular laser probe capable of functioning as both a straight and a curved laser probe. The probe includes an elongated handpiece and a rigid cannula fixed to the handpiece to prevent relative translational movement therebetween. An optical fiber for delivering laser energy extends through channels in the handpiece and cannula and is supported for translational movement therein. A slidable button is fixed to the optical fiber, via a rigid sleeve that supports the fiber such that the button and optical fiber move together in the same direction during operation. In this manner, the button may be retracted relative to the handpiece to retract the flexible fiber into the rigid cannula, thereby straightening the fiber, or the button may be advanced relative to the handpiece to extend the fiber from the cannula, thereby exposing the fiber and allowing it to curl into the curved tip configuration. Accordingly, retraction of the both the button and the handpiece in the same direction will cause the fiber to be retracted into the cannula and straightened as the tip of the fiber is withdrawn from the eye, thereby preventing possible damage to ocular tissue.

The fiber may be selectively positioned relative to the button to cause the button to act as a visual indicator of the direction in which the fiber will extend from the cannula. The button may be specially configured with an enlarged head portion to enhance grippability and smooth operation of the button.

DESCRIPTION OF THE DRAWINGS

FIG. 2 is a side view of an exemplary adjustable laser probe in accordance with one embodiment of the present invention;

FIG. 2A is an enlarged view of area B of FIG. 2;

FIG. 2B is a front end view of the laser probe of FIG. 2;

FIGS. 7A-7C are top, side and bottom views of an alternative embodiment of the button of the laser probe;

FIG. 8 is a side view of an alternative embodiment of a laser probe that includes the button of FIGS. 7A-7C; and FIG. 9 is a front end view of the laser probe of FIG. 8.

DETAILED DESCRIPTION

Figure 1A:
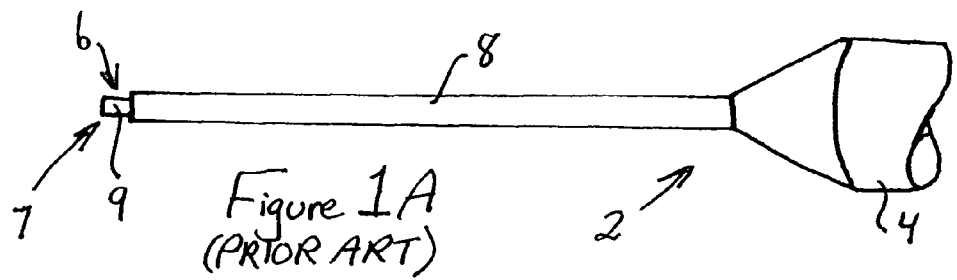
FIGS. 1A-1C are partial plan views of a laser probe of the prior art.
Figure 1B:
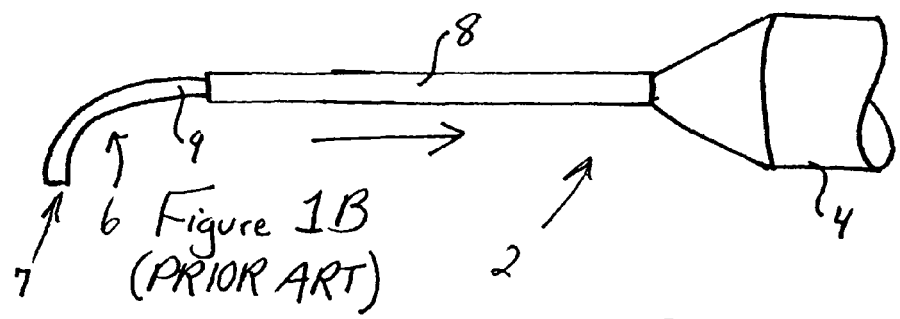
Figure 1C:
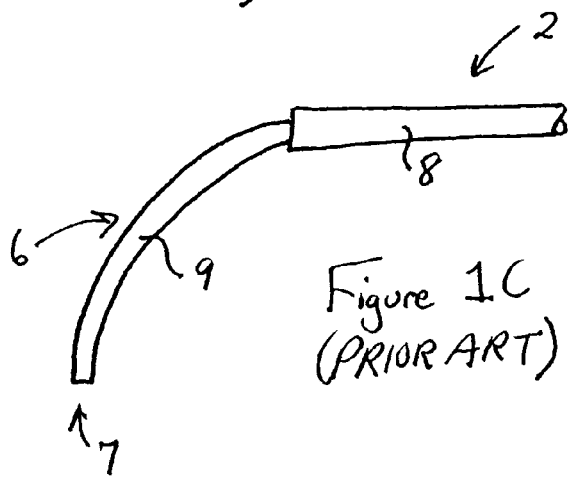
Figure 1D:
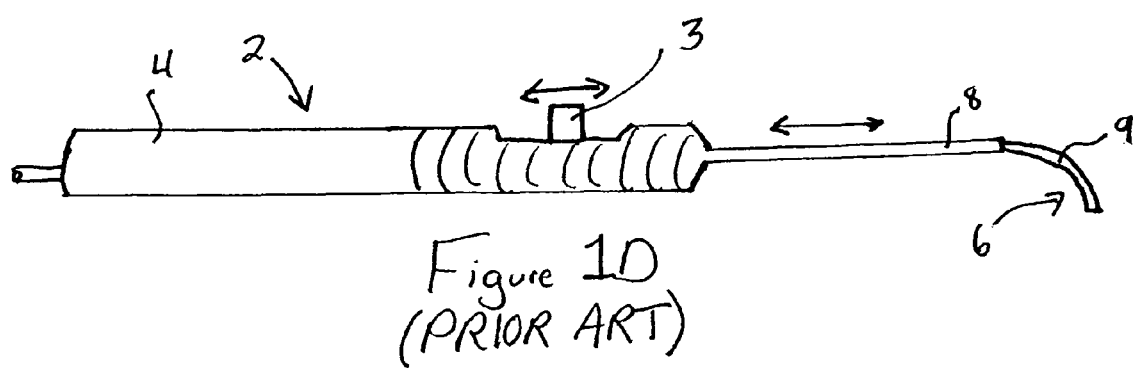
FIG. 1D is a plan view of the laser probe of FIG. 1A.

The present invention provides a laser probe providing adjustability between straight and curved configurations that eliminates disadvantages associated with the prior art. This laser probe improves the surgeon's ability to reach critical areas within the eye, provides for safer and intuitive surgical maneuverability, and allows for quick visual inspection to confirm proper probe orientation, before extension of the fiber to expose a curved tip.

The endo ocular laser probe of the present invention can function as both a straight and a curved laser probe. Referring now to FIG. 2, the probe 10 generally includes an elongated handpiece 12 and a rigid cannula 16 fixed to the handpiece 12 to prevent relative translational movement therebetween. An optical fiber 20 for delivering laser energy extends through channels in the handpiece 12 and cannula 16 and is supported for translational movement therein. A slidable button 22 is fixed to the optical fiber 20, such that the button 22 and optical fiber 20 move together in the same direction during operation. In other words, the button 22 may be retracted relative to the handpiece 12 to retract the flexible fiber into the rigid cannula 16, thereby straightening the fiber 20, or the button 22 may be advanced relative to the handpiece 12 to extend the fiber 20 from the cannula 16, thereby exposing the fiber 20 and allowing it to curl into the curved tip configuration, as shown in FIG. 2A. Accordingly, the button 22 is operable to "feed" or retract the fiber relative to the cannula 16 while the cannula 16 remains fixed in position relative to the handpiece. Operation of the probe, and control of the fiber relative to the handpiece, is thereby improved in a manner that is less likely to cause damage to a patient's ocular tissue during quick withdrawal from the eye as when a patient startles under anesthesia, etc. More specifically, retraction of the both the button 22 and the handpiece 12 in the same direction will cause the fiber to be retracted into the cannula 16. This causes the fiber's tip to be straightened during withdrawal from the eye, thereby preventing damage to ocular tissue. The fiber is selectively positioned relative to the button 22 to cause the button to act as a visual indicator of the direction in which the fiber will extend from the cannula, as shown in FIGS. 2A and 2B. The button 22 may be specially configured with an enlarged head portion 40 to enhance grippability and smooth operation of the button, as best shown in FIGS. 8 and 9.

The optical fiber 20 is a conventional type optical fiber. For example, two and one half (2.50) meters of length of a quartz optical fiber having a 200 micron diameter, including the light transmitting core 20a, a conventional buffer 20b and cladding 20c, has been found suitable (see FIG. 4). Optionally, additional cladding, such as a PVC sleeve 19, may be applied over the fiber/buffer/cladding to provide added durability, as best shown in FIGS. 2, 3 and 4.

Such optical fibers are typically straight or substantially straight when in a relaxed state. The diameter of the fiber may be selected according to the internal diameter of the cannula 16, or as otherwise necessary to be compatible with the desired incision size. The optical fiber 20 is preferably terminated at its proximal end 23 with a suitable connector, such as SMA connector 24, for connection to a laser source device, as shown in FIGS. 3 and 4. This may involve bonding the optical fiber 20 and/or any cladding to the connector by a suitable adhesive, such as cyanoacrylate, or as otherwise known in the art.

Figure 3:
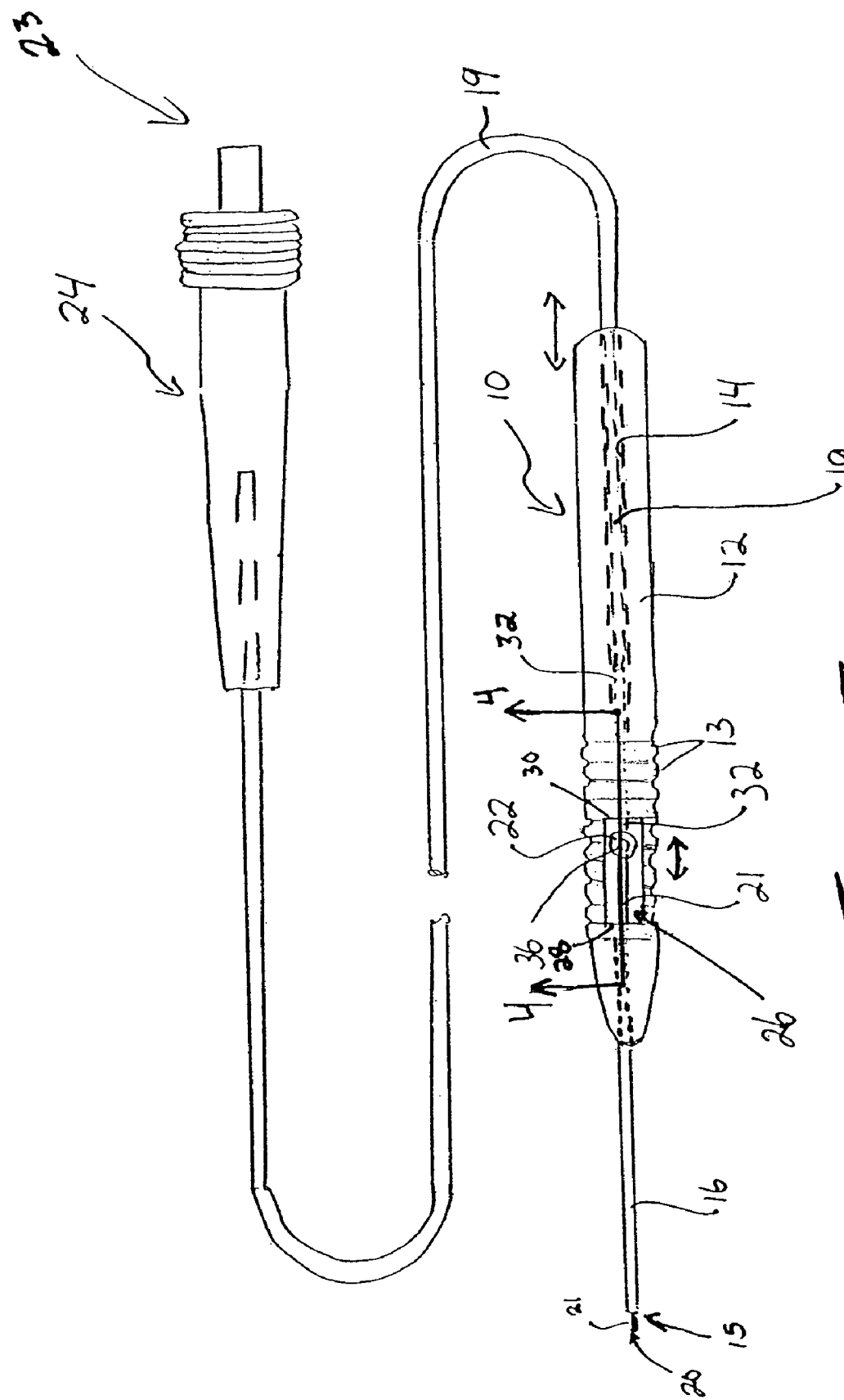
FIG. 3 is a top view of the laser probe of FIG. 2.
Figure 4:
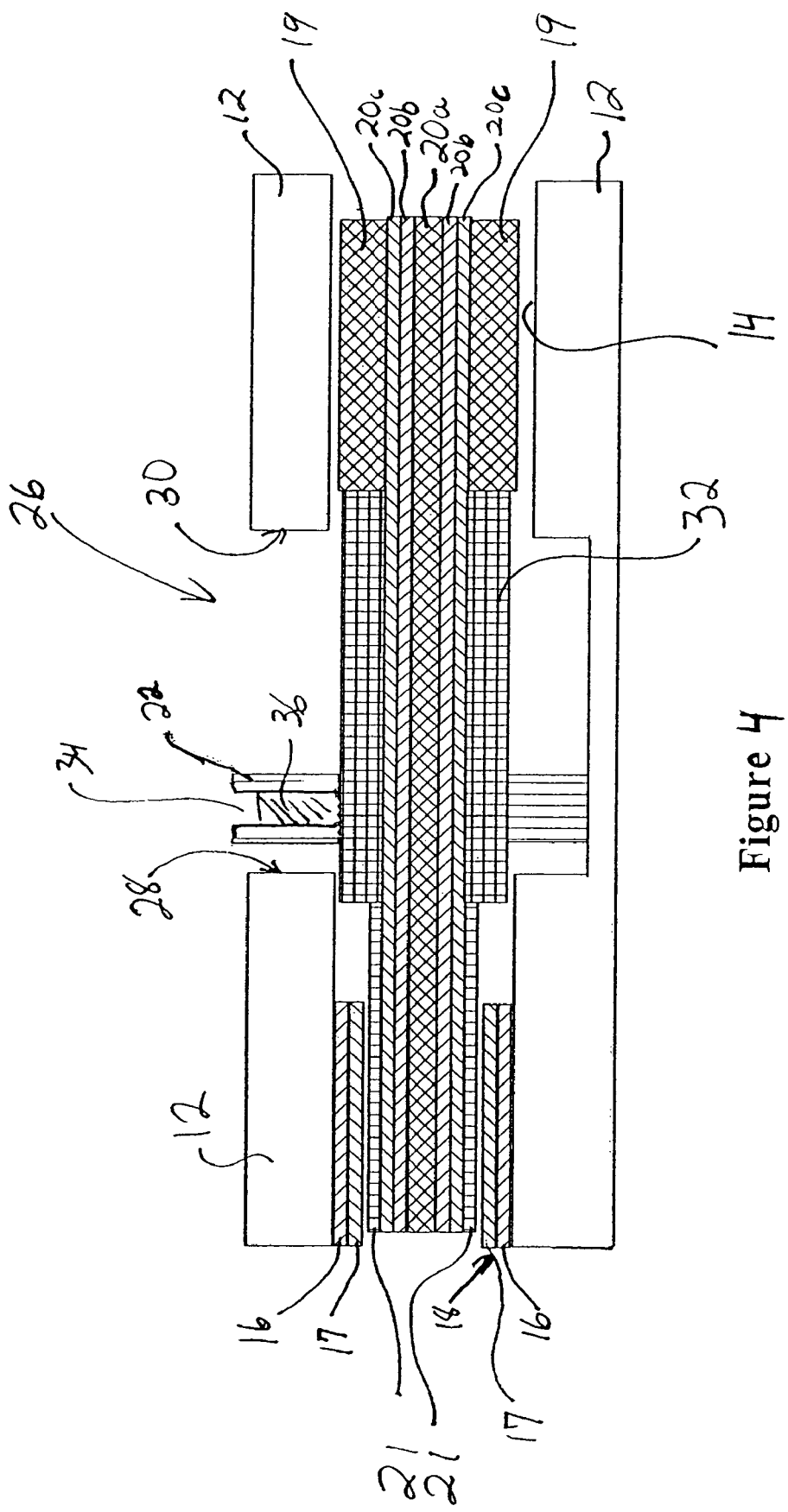
FIG. 4 is a partial cross-sectional view of the probe of FIG. 2, taken along line 4-4 of FIG. 3.

Referring now to FIGS. 2-5, it is further noted that the handpiece 12 defines an internal channel 14 extending therethrough this is dimensioned to receive the optical fiber, including the optical fiber's cladding, while permitting translational movement of the clad fiber within the channel 14 without substantial friction or other interference, as best shown in FIGS. 2-4. The handpiece 12 preferably defines a slotted portion 26, as generally known for prior art probes, as disclosed in U.S. Pat. No. 6,572,608 to Lee, and as shown in FIGS. 2, 3 and 4. The slotted portion 26 has a front wall 28 and a rear wall 30 for limiting translational movement of the button 22. The handpiece 12 may include external ridges 13 to facilitate secure grasping of the probe, as best shown in FIGS. 2 and 3.

The cannula 16 is rigid and is fixed to the handpiece 12 to prevent relative movement therebetween, as best shown in FIGS. 2 and 4. The cannula 16 defines an internal channel 18 substantially aligned with the channel 14 of the handpiece 12 and dimensioned to receive the optical fiber 20, including the core 20a, buffer 20b and cladding 20c, as covered by a resiliently deformable tube 21 capable of resiliently deforming between a bent/curved state and a straight state, so as to bend and straighten an otherwise straight optical fiber, as discussed further below. The rigid cannula 16 may be made of any suitable material, such as stainless steel. The cannula 16 may have any desired external diameter, such as to be compatible with a 20 g or 25 g stab incision commonly used in vitreo-retinal surgery.

Figure 5:
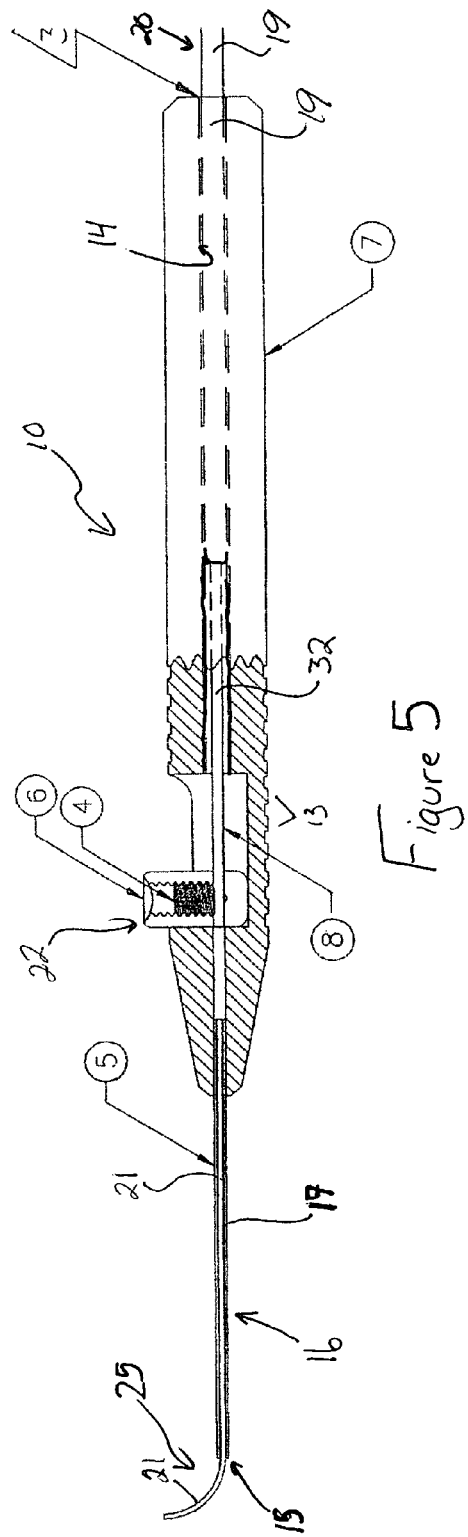
FIG. 5 is an enlarged side view of the laser probe of FIG. 2.
Figure 6:
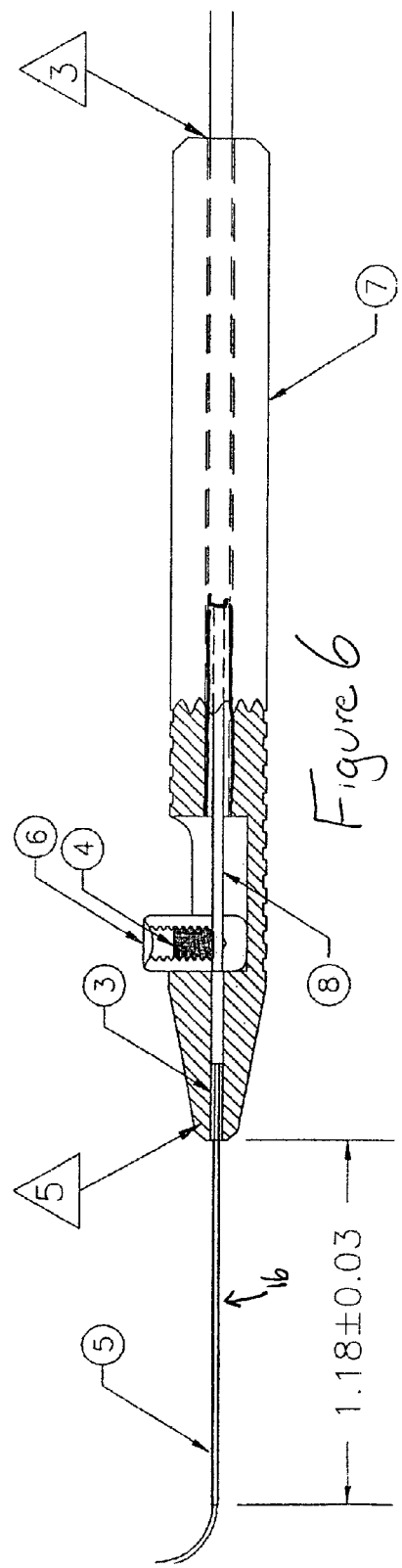
FIG. 6 is a side view of an alternate embodiment of a laser probe in accordance with the present invention.

Optionally, friction-reducing material, such as Teflon (polytetrafluoroethylene) or polyamide coating or tubing 17, is provided on or within an inner surface of the cannula 16, to reduce friction between the cannula 16 and the fiber 20, etc., and thereby facilitate extension and retraction of the fiber relative to the cannula 16, as best shown in FIGS. 2A and 4. For example, Teflon tubing 17 may be adhered to the internal surface of the cannula 16 by cyanoacrylate. In some embodiments, e.g. a 25 g embodiment, it may be preferable to exclude such friction-reducing material, due to manufacturing complexities, etc. Such an alternative embodiment is shown in FIG. 6. In either embodiment, the inner surface of the cannula 16, the fiber 20, and any flexible tube 21, as discussed further below, should be dimensioned to fit closely to present a substantially closed area at the distal tip 15 of the cannula 16 to prevent fluids from the eye or surgical procedure, etc. from entering the cannula 16, as best shown in FIGS. 2A, 3 and 5.

To provide for the curved tip configuration, the distal end portion 25 of the optical fiber 20 is enclosed in a resiliently deformable flexible tube 21 that has been pre-bent to an angle of about 90 degrees, such that the tube may be straightened, and yet will resiliently return to its pre-bent configuration, as best shown in FIGS. 2A and 4. For example, a nitinol tube 21 has been found suitable for this purpose. Nitinol, an acronym for Nickel Titanium Naval Ordnance Laboratory, is well known in the art, and describes a family of intermetallic materials that contain a nearly equal mixture of nickel (approx. 55 wt. %) and titanium. Other elements can be added to adjust or "tune" the material properties. Nitinol exhibits unique behavior, particularly shape memory, which is suitable for the flexible tube 21. Any other resiliently deformable material, such as a variety of plastic materials may be used, as will be appreciated by those skilled in the art. The flexible tube 21 is preferably bonded to the optical fiber 20, or more specifically to the fiber's outer cladding 20c, e.g. using a suitable adhesive such as cyanoacrylate, as best shown in FIG. 4. For example, the flexible tube 21 may be bonded with adhesive to the optical fiber 20 only at discrete points, e.g. adjacent the distal and proximal ends of the tube 21, to permit bending of the optical fiber 20 and flexible tube 21 along their lengths. For manufacturing or other considerations, the flexible tube 21 may enclose a length of the fiber extending from the distal end portion 25 to a portion just before (as shown in FIG. 4, or just after the point of attachment of the button 22.

The button 22 is fixed to the optical fiber 20 such that movement of the button 22 causes movement of the fiber in a like direction. In the embodiment shown in FIGS. 2 and 4, a length of the optical fiber 20 is stripped of its outer cladding 19 (typically a PVC material), and is enclosed in a rigid sleeve 32, such as stainless steel sleeve 32, as best shown in FIG. 4. This rigid sleeve 32 protects the integrity of the fiber 20 to prevent damage from attachment of the button 22 and advancing of the set screw 36. Additionally, the rigid sleeve 32 supports/stiffens the otherwise flexible to premit the fibres to be pushed/advanced from the handle with damage to the fibres, undue bending of the fiber, jamming of the fiber, etc. The optical fiber 20 (including any buffer 20b or cladding 20c) may be attached to the sleeve 32 by cyanoacrylate adhesive or other suitable means. The button 22 has a central bore 34 for receiving a threaded set screw 36 that can be advanced to fixedly attach the button 22 to the sleeve 32, as best shown in FIGS. 2, 3, 4 and 5. Alternatively, no adhesive is used and the set screw 36 crimps the sleeve 32 to attach it to the optical fiber 20. As yet another alternative, the button 22 may be adhesively or otherwise attached directly to the optical fiber 20 (or a portion thereof), without the need for a sleeve 32 or a set screw 36. Accordingly, the button 22, sleeve 32, flexible tube 21 and optical fiber 20 are fixed together such that longitudinal movement of the button 22 causes longitudinal movement of the optical fiber 20, etc. in a like direction.

The optical fiber 20, or more specifically at least a portion thereof, extends through the channel 14 of the handpiece 12 and into the cannula 16 and is supported for translational movement therein, as best shown in FIGS. 2 and 4. The button 22 rides within the slotted portion 26 of the handpiece 12 such that it is longitudinally moveable from an advanced position adjacent the front wall 28, in which the fiber extends from the cannula 16, as shown in FIGS. 2, 3, 4 and 5 and a retracted position adjacent the rear wall 30, in which the fiber is enclosed within the cannula 16.

Referring now to the alternative embodiment of FIGS. 8-9, the button 22 has a substantially cylindrical stem portion 38 joined to the fiber 20 (and sleeve 32) and extending in a radial direction relative to an axis of the cannula 16, and a head portion 40 joined to the stem portion 38, as shown in FIG. 7A-9. The head portion is enlarged to have having a top surface 42 area greater than a cross-sectional area of the stem portion 38. Preferably, the top surface has a length and a width that are both greater than a length and width of the stem portion, as best shown in FIGS. 7B, 7C, 8 and 9. Further, the top surface 42 may be configured with ridges 44, as best shown in FIGS. 7A, 7B and 8. The enlarged head 40 and ridges 44 enhance grip (friction relative to a surgeon's finger) and tend to facilitate smooth operation of the button. Additionally, the button 22 and handpiece 12 are preferably constructed of dissimilar materials (e.g. a Delrin (acetal resin) handpiece 12 and Polyetheretherketone (PEEK) button 22) to further enhance smooth operation. This can be particularly advantageous when friction reducing material 19 is not provided in the cannula 16, which results in increased friction in the cannula 16. Such an embodiment may be advantageous in small gauge (25 g) instruments in which such material 19 may be omitted for manufacturing or other reasons, such as the 25 g embodiment is shown in FIG. 6.

In an embodiment in which the probe includes a flexible tube 21 providing a curved tip configuration, when the distal end 25 of the optical fiber 20 is assembled within the handpiece 12, the flexible tube 21 protrudes from the cannula 16 to form the desired bend, e.g. a bend ranging from approximately 0° to approximately 90°, with a radius of approximately 0.1 to approximately 0.25 inches.

In a preferred embodiment, the flexible tube 21 is mounted on the optical fiber 20 and/or the optical fiber 20 is positioned relative to the handpiece 12, such that the optical fiber 20 will bend substantially in a central plane of the button 22, e.g. the plane of cross-section of FIGS. 2 and 8, and preferably toward the user-actuatable/head 40 portion of the button 22, as shown in FIGS. 2A, 2B, 8 and 9. In other words, the distal end portion 25 extends substantially within a plane when in an extended position, and the button 22 extends in a radial direction relative to an axis of the cannula 16 such that the radial direction extends substantially within the same plane, in substantially the same direction, such that the fiber bends toward the button 22 as shown in FIGS. 2A, 2B, 8 and 9, rather than away from the button as shown in FIG. 3 of U.S. Pat. No. 6,572,608. This positioning relationship between the flexible tube 21 and the button 22 provides the surgeon with a visual and tactile indication as to the direction in which the fiber 20 will bend when extended from the cannula 16. In other words, the button 11 provides a visual indication, while the distal end portion 25 is retracted and housed within the cannula 16, of where and in which direction the distal end portion 25 of the fiber 20 will extend when the button is advanced. This allows the surgeon to position the handpiece appropriately before extending the distal end portion to prevent damage to ocular tissue, etc. Additionally, should the surgeon need to adjust the button 22 when working inferio nasally, the button 22 will remain readily accessible as a result of the orientation of the button relative to the direction of curvature of the distal end portion of the fiber 20. Preferably, the button 22 is positioned relative to the optical fiber 20 and handpiece 12 such that there is no exposure of the optical fiber 20 or flexible tube 21 beyond the cannula 16 when the button 22 is completely retracted.

Accordingly, the probe 10 functions such that when the button 22 is moved distally (advanced), the optical fiber 20 advances and flexes toward its pre-bent curved shape, up to about 90 degrees and in line with the button 22. When the button 22 is moved proximally (retracted), the optical fiber 20 retracts into the non-flexible, stationary cannula 16 attached to the handpiece.

Optionally, the handpiece 12 and the optical fiber's external cladding 19 are made of translucent materials. For example, white Delrin (acetal resin) and white PVC have been found to be suitable for the handpiece and cladding, respectively. This allows for visual inspection of the optical fiber/probe for defects or discontinuities in the optical fiber or inconsistencies in performance when laser source is used that propagates light of a wavelength visible to the human eye. Specifically, such defects or discontinuities will allow escape of some laser light, which will be readily apparent upon visual inspection as a glow at the point of the defect, e.g. a green glow when a green argon laser is used.

Accordingly, the present invention provides a laser probe that does not require the surgeon's finger to remain on the button at all times, as is recommended for prior art probes, and yet the longitudinal position and directional orientation of the distal end of the optical fiber remains satisfactorily stable and/or predictable. Additionally, the inventive laser probe allows for the retraction of the laser fiber by retracting the button, an intuitive movement, followed by retraction of the instrument from the eye.

In a preferred embodiment, the laser probe is therefore adjustable in that it allows for operation in both straight and curved tip configurations, intuitive in that retracting the button retracts the optical fiber, stable in that the stationary sheath alleviates the need for the surgeon to maintain a finger positioned on the slidable button, informative in that it can be configured such that the button position provides a visual or tactile indication of the direction in which the flexible laser fiber will extend, universal in that it can be configured with any suitable connector for attachment to any suitable laser source, versatile in that it can be produced with cannulas of various sized to accommodate 20 g, 25 g or other desired tip sizes, and visually verifiable in that the laser probe and/or fiber cladding can be constructed of a translucent material to allow for inspection for escape of light in order to detect any functionality issues with the probe, such as broken fibers, tissue coagulation on the probe tip, or a faulty laser source device.

Having thus described particular embodiments of the invention, various alterations, modifications, and improvements will readily occur to those skilled in the art. Such alterations, modifications and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed:

1. A surgical probe comprising:
   a handpiece defining a first internal channel;
   a rigid cannula fixed to said handpiece to prevent relative translational movement therebetween, said cannula having a second internal channel extending to a distal tip;
   an optical fiber extending through said first and second internal channels, said optical fiber having a distal end portion positionable adjacent said distal tip, said distal end portion having a preformed bend that is straightened in a retracted position within said rigid cannula, and that is curved when in an extended position in which said distal end portion extends beyond said distal tip of said rigid cannula;
   a mechanism that selectively causes translational movement of said optical fiber relative to said handpiece, thereby causing said distal end portion of said optical fiber to move between said retracted and extended positions; and
   a rigid sleeve enclosing at least a portion of said optical fiber, said mechanism being attached to said rigid sleeve, said rigid sleeve supporting said optical fiber and being capable of translating with said optical fiber upon operation of said mechanism.

2. The surgical probe of claim 1, said mechanism comprising a button fixedly attached to said optical fiber, said button being selectively translatable to cause corresponding translational movement of said optical fiber relative to said handpiece, thereby causing said distal end portion of said optical fiber to move between said retracted and extended positions, said button extending in a radial direction relative to an axis of said cannula.

3. The surgical probe of claim 2, wherein said distal end portion extends substantially within a plane when in said extended position, and wherein said radial direction extends substantially within said plane, substantially in said radial direction.

4. The surgical probe of claim 3, wherein said handpiece is constructed of a first material, said optical fiber is positioned within said first internal channel without any material intermediate said first material and said optical fiber, and wherein said button is constructed of a second material different from said first material.

5. The surgical probe of claim 4, wherein said first material comprises acetal resin said second material comprises polyetheretherketone.

6. The surgical probe of claim 5, said optical fiber having a core and wherein said distal end portion of said core of said optical fiber is enclosed in a resiliently deformable flexible tube constructed of a shape memory material.

7. The surgical probe of claim 6, wherein said tube is constructed of nitinol.

8. A surgical probe comprising:
a handpiece defining a first internal channel;
a rigid cannula fixed to said handpiece to prevent relative translational movement therebetween, said cannula having a second internal channel extending to a distal tip;
an optical fiber extending through said first and second internal channels, said optical fiber having a distal end portion positionable adjacent said distal tip, said distal end portion having a preformed bend that is straightened when in a retracted position within said rigid cannula, and that is curved when in an extended position in which said distal end portion extends beyond said distal tip of said rigid cannula, said distal end portion extending substantially within a plane when in said extended position;
a button fixedly attached to said optical fiber, said button being selectively translatable to cause corresponding translational movement of said optical fiber relative to said handpiece, thereby causing said distal end portion of said optical fiber to move between said retracted and extended positions, said button extending in a radial direction relative to an axis of said cannula, said radial direction extending substantially within said plane, substantially in said radial direction; and
a rigid sleeve enclosing a portion of said optical fiber, said button being attached to said rigid sleeve, said rigid sleeve supporting said optical fiber and being capable of translating with said optical fiber and said button upon translation of said button.

9. The surgical probe of claim 8, wherein said rigid sleeve is adhesively bonded to a portion of said optical fiber.

10. The surgical probe of claim 9, wherein said button is mechanically fastened to said rigid sleeve.

11. The surgical probe of claim 8, said button comprising a stem portion joined to said fiber extending in a radial direction relative to an axis of said cannula, said button further comprising a head portion joined to said stem portion, said head having an area greater than a cross-sectional area of said stem portion.

12. A surgical probe comprising:
a handpiece defining a first internal channel;
a rigid cannula fixed to said handpiece to prevent relative translational movement therebetween, said cannula having a second internal channel extending to a distal tip;
an optical fiber extending through said first and second internal channels, said optical fiber having a core and a distal end portion positionable adjacent said distal tip, said distal end portion having a preformed bend that is straightened when in a retracted position within said rigid cannula, and that is curved when in an extended position in which said distal end portion extends beyond said distal tip of said rigid cannula;
a button fixedly attached to said optical fiber, said button being selectively translatable to cause corresponding translational movement of said optical fiber relative to said handpiece, thereby causing said distal end portion of said core to move between said retracted and extended positions, said button comprising a stem portion joined to said fiber extending in a radial direction relative to an axis of said cannula, said button further comprising a head portion joined to said stem portion, said head having an area greater than a cross-sectional area of said stem portion; and
a rigid sleeve enclosing a portion of said optical fiber, said button being attached to said rigid sleeve, said rigid sleeve supporting said optical fiber and being capable of translating with said optical fiber and said button upon translation movement of said button.

13. The surgical probe of claim 12, wherein said rigid sleeve is adhesively bonded to a portion of said optical fiber.

14. The surgical probe of claim 13, wherein said head portion comprises a plurality of ridges extending in a direction transverse to a direction of elongation of said handpiece.

15. The surgical probe of claim 14, wherein said distal end portion extends substantially within a plane when in said extended position, and wherein said radial direction extends substantially within said plane, substantially in said radial direction.

16. The surgical probe of claim 14, wherein said handpiece is constructed of a first material, said optical fiber is positioned within said first internal channel without any material intermediate said first material and said optical fiber, and wherein said button is constructed of a second material different from said first material.

17. The surgical probe of claim 16, wherein said first material comprises acetal resin and said second material comprises polyetheretherketone.

18. The surgical probe of claim 12, wherein said distal end portion of said core of said optical fiber is enclosed in a resiliently deformable flexible tube constructed of a shape memory material.

19. The surgical probe of claim 18, wherein said tube is constructed of nitinol.

20. The surgical probe of claim 19, wherein said cannula has an interior surface and a layer of friction-reducing material between said interior surface and said optical fiber.

21. A surgical probe comprising:
a handpiece defining a first internal channel;
a rigid cannula fixed to said handpiece to prevent relative translational movement therebetween, said cannula having a second internal channel extending to a distal tip;
an optical fiber extending through said first and second internal channels, said optical fiber having a distal end portion positionable adjacent said distal tip, said distal end portion having a preformed bend that is straightened in a retracted position within said rigid cannula, and that is curved when in an extended position in which said distal end portion extends beyond said distal tip of said rigid cannula;
a mechanism that selectively causes translational movement of said optical fiber relative to said handpiece, thereby causing said distal end portion of said optical fiber to move between said retracted and extended positions; and
a rigid sleeve attached to said optical fiber and enclosing at least a portion of said optical fiber, said mechanism being attached to said rigid sleeve, said rigid sleeve being capable of translating with said optical fiber upon operation of said mechanism.

22. The surgical probe of claim 21, wherein said rigid sleeve is attached to said optical fiber by adhesive.

23. The surgical probe of claim 21, wherein said rigid sleeve is attached to said optical fiber by a screw.

24. The surgical probe of claim 21, wherein said rigid sleeve encloses only a portion of said optical fiber.

* * * * *